United States Patent [19]

Garrett et al.

[11] 4,160,033
[45] Jul. 3, 1979

[54] METHOD FOR THE CONTROL OF MOSQUITOS BY THE USE OF FILM-FORMING MATERIALS

[75] Inventors: William D. Garrett, Oxon Hill; William R. Barger, Camp Springs, both of Md.

[73] Assignee: The United States of America as represented by the Secretary of the Navy, Washington, D.C.

[21] Appl. No.: 764,310

[22] Filed: Jan. 31, 1977

[51] Int. Cl.$^2$ .......................... A01N 9/28; A01N 9/24
[52] U.S. Cl. .................................. 424/285; 424/342
[58] Field of Search ............... 424/283, 342, 172, 343, 424/285; 252/351; 210/59

[56] References Cited

U.S. PATENT DOCUMENTS

| 3,639,255 | 2/1972 | Boardman et al. | 252/351 |
| 3,740,419 | 6/1973 | Campbell | 421/21 |

OTHER PUBLICATIONS

McMullen et al., Nature 234,51 (1971).
Lorenzen et al., Mosq. News, 28, 187 (1968).
Atlas Technical Bulletin I, Atlas Chemical Industries, 1963.
Atlas Technical Bulletin II, Atlas Chemical Industries.
Manzelli, Proc. N.J., Mosq. Exterm. Assoc. 28, 19 (1941).
Singh et al., Mosq. News 17, 70 (1957).
Wiltzius, "Effects of Monolayers on Insects, Fish, and Wildlife", Research Report No. 7, Bureau of Reclamation (1967).
Milla et al., Mosq. News, 28, 187 (1968).
Chem. Abst. vol. 82, 90681t (1975).
Chem. Abst. (A), 8th Collective Index, vols. 66–75, (1967–1971).
Chem. Abst. (B), vol. 74, 3068s (1971).
Griffen, W. C., The American Perfurmer and Essential Oil Review, May 1955, pp. 26–29.
Garrett, W. D., Mosquito Control in the Aquatic Environment with Monomolecular Organic Surface Films; NRL Report 8020, NRL Jul. 16, 1976.

Primary Examiner—Albert T. Meyers
Assistant Examiner—H. Steven Seifert
Attorney, Agent, or Firm—R. S. Sciascia; Philip Schneider; Thomas McDonnell

[57] ABSTRACT

A method of controlling mosquitos by adsorbing onto the surface of a body of water suitable for breeding mosquitos a monomolcular or duplex film of an organic material which reduces the surface tension of the body of water to 30 dynes/cm or less.

7 Claims, No Drawings

METHOD FOR THE CONTROL OF MOSQUITOS BY THE USE OF FILM-FORMING MATERIALS

BACKGROUND OF THE INVENTION

This invention pertains generally to mosquito control and in particular to a nonpoisonous mosquito larvae and pupae control.

A common approach to mosquito control is to prevent the emergence of the adult from its aquatic breeding site through the application of a water-immiscible, organic chemical which forms a film on the water. It is necessary for these film-forming chemicals and the surface films which they form to have certain physicochemical properties to ensure not only effectiveness against aquatic forms of mosquito, but also ease of application and persistence. The chemicals must be nonionic, nonvolatile, and water immiscible liquids. Furthermore, the chemicals and the resulting films must have a low freezing point, be commercially available at a reasonable cost, and be nontoxic and be noncorrosive. It is also necessary for the surface film to be fluid with rapid and spontaneous spreading and with high respreading potential.

Unfortunately, the presently used compounds fail to have one or more of these properties. Petroleum-based oils have, in general, the disadvantages of fouling the shore areas, killing other marine life and vegetation, and extra cost due to a large usage requirement. The nonvolatile hydrocarbon component of these films containing only alkanes and cycloalkanes are slow in their impact on larvae. The more rapid toxic effects are obtained from volatile aromatics and other toxic compounds contained in these films which are drawn into the larvae breathing trachae during respiration. However, these compounds have poor resistance because of their volatility and often are toxic to too many other aquatic creatures.

SUMMARY OF THE INVENTION

It is, therefore, an object of this invention to provide a nontoxic and environmentally safe control of mosquitos.

Another object of this invention is to provide a method of controlling mosquitos which has little difficulty in application and produces persistent results.

A further object of this invention is to provide an economical method of controlling mosquitos.

These and other objects are achieved by the adsorption to the surface of the water of a nonionic, autophobic or nearly autophobic, immiscible, nonvolatile fluid which has a density less than that of water and high degrees of fluidity and which is capable of reducing the surface tension of the water to 30 dynes/cm or less, so that the immature forms of mosquito are prevented from attaching themselves to the surface of the water by a persistant biologically inert means which is only one molecule thick or, on the average, greater than one but less than twenty molecules thick.

DETAILED DESCRIPTION OF THE INVENTION

The monomolecular or duplex films of this invention are adsorbed to the water surface by adding to the water a compound or composition described below at a surface concentration of 80 microliters/square meter of surface or less and preferably 40 microliters/square meter of surface or less. A surface concentration of 40 $\mu l/m^2$ is about 20 times greater than that required for monomolecular layer. Consequently, the lower limit to the above ranges would be about two microliters per square meter for a monomolecular film covering the entire water surface. The excess allows the film to be replenished automatically when the need arises. It should be noted that even if the entire surface is no longer convered by the monomolecular film of this invention the film would continue to eradicate the immature forms of mosquitos in the portions of surface which are still covered.

The compounds encompassed by the practice of the present invention are nonionic and autophobic or nearly autophobic. An autophobic material is one which does not spread over its own monomolecular films. An excess of the material remains concentrated at the point of addition. The nearly autophobic compounds generally come from the small impurities present in the commercial grade of many of the compounds encompassed by the present invention. The impurities compromise the autophobicity of the compounds with the result that the films varies in thickness from one molecule to several molecules. This latter type of film is referred to as a duplex film. The duplex films behave in the same manner as the monomolecular films. In fact, if the amount of material added to the surface of the water is equal to or less than that required to cover the surface with a monomolecular layer, the film which would otherwise be duplex would be monomolecular.

The compounds of this invention have a density of less than that of water, a freezing point of less than 5° C., a boiling point of 170° C. or higher and preferably of 200° C. or higher, an HLB number of 10 or less and preferably of 6 or less, and a bulk viscosity of less than 1000 centistokes at the temperature of use and preferably less than 200 centistokes. The fluidity of the compound solutions is such that the compounds or solutions have a spreading velocity of 10 cm/sec for the first 100 cm and preferably 14 cm/sec for the first 100 cm. Most importantly, the compounds reduce the surface tension of the water to 30 dynes/cm or less. This particular combination provides a means of lowering the surface tension which is persistent enough to be used in many environments.

The preferred compounds or compositions for the practice of this invention are: sorbitan monooleate, a solution of 70 volume percent to less than 100 volume percent of sorbitan monooleate and 2-ethyl butanol; saturated, branched chain alcohols with a total carbon from 15 to 19 carbon atoms and one to three oxyethylene groups; unsaturated cis alcohols with 15 to 19 carbon atom chain length; unsaturated ethers with a chain length of 12 to 18 carbon atoms and three to five oxyethylene groups; and oleyl ether with two oxyethylene groups. Combinations of any of the above compounds are useful. The most preferred compounds or compositions are: sorbitan monooleate; a solution of 75 volume percent of sorbitan monoleate; and 25 volume percent of 2-ethyl butanol; isostearyl alcohol with two oxyethylene groups; lauryl ether with four oxyethylene groups; a solution comprising 50 volume percent of sorbitan monooleate and 50 volume percent of lauryl ether with four oxyethylene groups; and oleyl ether with two oxyethylene groups.

In order to demonstrate the practical utility of this invention, the following examples are given. It is understood that these examples are given by way of illustration and are not intended to limit this disclosure.

EXPERIMENT I

Distilled water was covered with a film of liquid in equilibrium with a small excess lens. Surface tensions were measured at 25° C. by the ring method using a Kruss du Nouy tensiometer. Surface tensions of the film-covered water remained essentially constant over a period of 24 hours for the liquid compounds and formulations used in this research shown in Table 1.

Table 1

| | Monomolecular Organic Surface Films and Surface Tensions | | |
|---|---|---|---|
| Liquid | Film Composition | Surface Tension N/m | dyn/cm |
| A | Diethylene glycol monolaurate | 0.0276 | 27.6 |
| B | Sorbitan monooleate, 75%; 2-ethyl butanol, 25% | 0.0289 | 28.9 |
| C | Sorbitan monooleate, 37.5% lauryl ether containing 4 oxyethylene groups, 50% 2-ethyl butanol, 12.5% | 0.0283 | 28.3 |
| D | Isostearyl alcohol containing 2 oxyethylene groups | 0.0282 | 28.2 |
| E | Lauryl ether containing 4 oxyethylene groups | 0.0271 | 27.1 | major carrier of malaria and the *Aedes aegypti* is the major carrier of yellow fever.

II

Influence of Surface Films on *Anopheles quadrimaculatus*

Films of liquids, A,B,C, and D were spread over water in polyethylene-lined trays (25×51 cm) in the laboratory and onto the surface of four similar ponds in a natural paludal setting. An additional control tray and pond were maintained in both laboratory and field experiments, with the exception of the terminal studies where the control organisms were treated with a film of isostearyl alcohol (2 oxyethylene groups) to provide additional data. Fourth-instar larvae of *Anopheles quadrimaculatus* had been placed into the trays and ponds several hours prior to application of the film-forming liquids to allow time for the larvae to adjust to the new environment. The field ponds had a surface area of about 4 $m^2$ and were created in a drainage ditch with wooden barriers to segregate the five equal areas. The ponds were lined with polyethylene sheet to prevent water and chemical exchange between them and to facilitate larval mortality counts. The results are given in Tables 2, 3, and 4.

Table 2

Laboratory Data, Effect on Monomolecular Films on Immature Stages of *Anopheles Quadrimaculatus*

| Liquid | Film Composition | Number Larvae Pupae Used | Cumulative Mortality After Indicated Hours of Posttreatment Exposure | | | Percent total Mortality |
|---|---|---|---|---|---|---|
| | | | Hours | Larvae | Pupae | |
| A | Diethylene glycol monolaurate | 322 Larvae | 24 | 247 | 0 | 76.7 |
| | | | 48 | 264 | 1 | 82.3* |
| | | | 72 | 269 | 1 | 83.8 |
| B | Sorbitan monooleate, 75% 2-ethyl butanol, 25% | 100 Larvae | 24 | 95 | 0 | 95.0 |
| | | | 48 | 95 | 0 | 95.0 |
| | | | 72 | 95 | 0 | 95.0 |
| B | Sorbitan monooleate, 75% 2-ethyl butanol, 25% | 93 Pupae | 24 | | 13 | 56.5 |
| | | | 28 | | 13 | 56.5+ |
| C | Sorbitan monooleate, 37.5% Lauryl ether (4 oxyethylene groups) 50% 2-ethyl butanol, 12.5% | 435 Larvae | 24 | 435 | 0 | 100.0 |
| D | Isostearyl alcohol (2 oxyethylene groups) | 462 Larvae | 24 | 462 | 0 | 100.0 |
| D | Isostearyl alcohol (2 oxyethylene groups) | 25 Pupae | 24 | | 25 | 100.0 |
| Controls | | 462 Larvae | 24–72 | 0 | 0 | 0.0 |

*one(1) Adult successfully eclosed after 48 hrs.
+Two(2) (2) and eight(8) adults successfully eclosed after 24 and 28 hrs, respectively Pupae has been added to SMO 75/2EB used in previous study with 100 larvae; film was 20 hrs old at time of emplacement.

EXPERIMENTS II & III

In both laboratory and field experiments the films were applied at a surface concentration of 40 $\mu l/m^2$. This value is about 20 times that required for a single monomolecular layer, and was used to provide an excess of chemical to resupply losses from the film. The excess material did not spread over its own film, but remained as an unspread patch or liquid lens which acted as a reservior to maintain complete coverage of the water surface. In order to test the breadth of effective of the compounds of Table 1, *Anopheles quadrimaculatus* and *Aedes aegypti* were treated. These two species of mosquitos are two of the most deadly species of mosquitos. The *Anopheles quadrimaculatus* is the Table 3

Laboratory Data, Rapid Effect on Monomolecular Films on Larval Stages of *Anopheles quadrimaculatus*

| Liquid | Film Composition | Time (Min) | Live Larvae |
|---|---|---|---|
| C | Sorbitan monooleate, 37.5% Lauryl ether (4 oxyethylene groups), 50% 2-Ethyl butanol, 12.5% | 0 | 25 |
| | | 7 | 10 |
| | | 13 | 4 |
| | | 15 | 1(3rd instar) |
| B | Sorbitan monooleate, 75% 2-Ethyl butanol, 25% | 0 | 100 |
| | | 16 | 16 |
| | | 26 | 7 |
| | | 41 | 5(3rd instar) |
| D | Isostearyl Alcohol (2 oxyethylene groups) | 0 | 462 |
| | | 15 | 20 |

Table 3-continued

Laboratory Data, Rapid Effect on Monomolecular Films on Larval Stages of Anopheles quadrimaculatus

| Liquid | Film Composition | Time (Min) | Live Larvae |
|---|---|---|---|
|  |  | 20 | 3 (3rd instar) |
|  |  | 35 | 3 |
|  |  | 45 | 1 |
|  |  | 24 hrs | 0 |

Table 4

Field Anopheles Effect of Monomolecular Films on Larval Stages of Anopheles quadrimaculatus*

| Liquid | Film Composition | Hours of Exposure | Cumulative Larval Mortality | Percent Total Mortality |
|---|---|---|---|---|
| A | Diethylene glycol monolaruate | 24 | 3554 | 71.1 |
|  |  | 48 | 3786 | 75.7 |
|  |  | 72 | 4065 | 81.3 |
|  |  | 120 | 4942(*) | 98.8 |
| B | Sorbitan monooleate, 75% 2-ethyl butanol, 25% | 24 | 5000 | 100.0 |
| C | Sorbitan monooleate, 37.5% | 24 | 3850 | 77.0 |
|  | Lauryl ether (4 oxyethylene groups), 50% | 48 | 4156 | 83.1 |
|  |  | 72 | 4365 | 87.3 |
|  | 2-ethyl butanol, 12.5% | 120 | 4842 | 96.8 |
| D | Isostearyl alcohol (2 oxyethylene groups) | 24 | 10,000+ | 100.0 |
|  | Controls | 24 | 0 | 0.0 |
|  |  | 48 | 0 | 0.0 |
|  |  | 72 | 55 | 1.1 |

*Observed mortality after 72 hrs may be partially due to unknown causes. Water striders were active on pools 48 hrs after treatment. No controls available for comparison after 72 hrs.
+Reflects the results of two(2) replicates 5,000 larvae each.

III

Surface Film Effects on Aedes aegypti

The experimental procedure of Example II was repeated with this species of mosquito.

The larvae, pupae, and emerging adults were adversely affected by monomolecular films of the tested compounds, but not to the same degree as the Anopheles quadrimaculatus was. The results are summarized in the following table.

Table 5

Influence of Monomolecular Surface Films on Pupae and Emerging Adults of Aedes aegypti

| Surface Film | Number of Pupae | 24 Hour Mortality | | | 48 Hour Mortality | | |
|---|---|---|---|---|---|---|---|
|  |  | Pupae | Adults | Percent* | Pupae | Adults | Percent* |
| Isostearyl alcohol containing two oxyethylene groups | 96 | 78 | 0 | 81.2 | 93 | 3 | 100 |
| Sorbitan monooleate, 75% 2-ethyl butanol, 25% | 124 | 88 | 7 | 76.6 | 89 | 31 | 96.8+ |
| Lauryl ether containing four oxyethylene groups | 80 | 80 | 0 | 100 | 80 | 0 | 100 |
| Sorbitan monooleate | 106 | 81 | 10 | 85.8 | 81 | 25 | 100 |
| Control | 50 | 0 | 0 | 0 | 1 | 0 | 2 |

*Percent total mortality (pupae and adults).
+Four successful eclosions.

As the experimental results prove, the organic films of the present invention produce a highly effective means for eradicating immature forms of mosquitos and thus mosquitos themselves. Since the compounds of the present invention do kill the immature forms of mosquitos by reducing the surface tension of the water so that the larvae and pupae sink and drown, rather than by suffocation or poisoning, relatively small amounts are needed and little or no harm occurs to the other forms of aquatic life. Consequently, the compound provides the most environmently safe means for eradicating mosquitos.

The present invention was first reported in detail in Garrett, W. D. *Mosquito Control in the Aquatic Environment with Monomolecular Organic Surface Films.* NRL Report 8020. NRL, July 16, 1976. This report is herein incorporated by reference.

Obviously many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. A method for eradicating mosquitos by applying to a body of water containing immature forms of mosquitos, in an amount sufficient to provide and maintain an approximately monomolecular film of a nonionic, autophobic, organic material with a density less than that of water, a boiling point of 170° C. or higher, a freezing point of less than 5° C., an HLB number of 10 or less, a bulk viscosity of less than 1000 centistokes at the temperature of use, a spreading velocity of 10 cm/sec for the first 100 cm, and a surface tension effectiveness which lowers the surface tension of said body of water to 30 dynes/cm or less.

2. The method of claim 1 wherein said material has a bulk viscosity of 200 centistokes or less at the temperature of use and a boiling point of 200° C. or more.

3. The method of claim 1 wherein said material is applied in an amount sufficient to provide a surface concentration from about 2 $\mu l/m^2$ to 80 $\mu l/m^2$.

4. The method of claim 1 wherein said material has a boiling point of 200° C. or higher, an HLB number of 6 or less, a bulk viscosity of less than 200 centistokes, and a spreading velocity of 14 cm/sec for the first 100 cm and said material is added in an amount sufficient to provide a surface concentration from about 2 $\mu l/m^2$ to 40 $\mu l/m^2$.

5. The method of claim 1 wherein said material is selected from the class consisting of sorbitan monooleate; a solution of 70 volume percent to less than 100 volume percent of sorbitan monooleate and 2-ethyl butanol; saturated, branched-chain alcohols with a carbon total from 15 to 19 carbon atoms, and one to three oxyethylene groups; unsaturated cis-alcohols with a 15 to 19 carbon atom chain length; unsaturated ethers with a chain length of 12 to 18 carbon atoms and three to five oxyethylene groups; and oleyl ether with two oxyethylene groups and mixtures thereof.

6. The method of claim 1 wherein said material is selected from the class consisting of sorbitan monooleate; a solution of 75 volume percent of sorbitan monooleate; and 25 volume percent of 2-ethyl butanol, isostearyl alcohol with two oxyethylene groups; lauryl ether with four oxyethylene groups; a solution comprising 50 volume percent of sorbitan monooleate and 50 volume percent of lauryl ether with four oxyethylene groups; and oleyl ether with two oxyethylene groups.

7. The method of claim 1 which further comprises repeating the addition of said material every 24 hours.

* * * * *